United States Patent [19]

Sievers et al.

[11] Patent Number: 4,717,675
[45] Date of Patent: Jan. 5, 1988

[54] METHOD FOR SELECTIVE CONVERSION OF ORGANIC COMPOUNDS AND DETECTING SAME BY GAS CHROMOTOGRAPHY AND CHEMILUMINESCENCE DETECTION

[75] Inventors: Robert E. Sievers; Stefan A. Nyarady, both of Boulder, Colo.

[73] Assignee: Sievers Research, Inc., Boulder, Colo.

[21] Appl. No.: 810,883

[22] Filed: Dec. 17, 1985

Related U.S. Application Data

[63] Continuation of Ser. No. 637,505, Aug. 3, 1984, abandoned.

[51] Int. Cl.$^4$ ............................................. G01N 21/76
[52] U.S. Cl. .................................... 436/103; 436/117; 436/118; 436/172; 436/159
[58] Field of Search ................. 436/35, 116, 117, 118, 436/158, 159, 131, 132, 142, 172, 175, 111, 103, 104; 422/52, 89, 78, 80; 423/405; 568/401, 402, 403, 436, 478, 487, 489; 585/627, 411; 502/344

[56] References Cited

U.S. PATENT DOCUMENTS

| | | | |
|---|---|---|---|
| 2,164,826 | 7/1940 | Langwell et al. | 75/118 |
| 3,365,498 | 1/1968 | Bryant et al. | 568/401 |
| 3,380,934 | 4/1968 | Batzold | 252/462 |
| 3,553,220 | 1/1971 | Etherington | 502/344 X |
| 3,725,482 | 4/1973 | Cant et al. | 568/478 |
| 3,870,468 | 3/1975 | Neti . | |
| 3,882,028 | 5/1975 | Zolner | 250/361 |
| 3,919,397 | 11/1975 | Gould | 423/405 |
| 3,963,928 | 6/1976 | Zolner | 250/361 C |
| 4,028,274 | 6/1977 | Kunz | 252/447 |
| 4,066,409 | 1/1978 | Fine . | |
| 4,066,411 | 1/1978 | Fine et al. . | |
| 4,154,762 | 5/1979 | Huang et al. | 568/402 |
| 4,162,235 | 7/1979 | Acres et al. | 252/462 |
| 4,193,963 | 3/1980 | Bruening | 422/52 |
| 4,301,114 | 11/1981 | Rounbehler et al. | 422/52 |

OTHER PUBLICATIONS

Fine, David H. et al., "Description of the Thermal Energy Analyzer (TEA) for Trace Determination of Volatile & Nonvolatile N-Nitroso Compounds", *Analytical Chemistry*, vol. 47, No. 7, (Jun. 1975) pp. 1188-1191.

Fontijn, A. et al., "Homogeneous Chemiluminescent Measurement of Nitric Oxide with Ozone", *Analytical Chemistry*, vol. 42, No. 6 (May 1970) pp. 575-579.

Cocco, G. et al., "Chemical Reactivity of Supported Gold. A Structural Study by Small-Angle X-ray Scattering & X-ray Absorption Spectroscopy", *Journal of Physical Chemistry*, vol. 83, No. 19, 1979, pp. 2527-2537.

S. Galvagno et al., "Chemical Reactivity of Supported Gold, IV, Reduction of NO by $H_2$", Journal of Catalysis, vol. 55, (1978) pp. 178-190.

M. J. Bollinger et al., "Conversion of Nitrogen Dioxide, Nitric Acid, & n-Propyl Nitrate to Nitric Oxide by Gold-Catalyzed Reduction with Carbon Monoxide", *Analytical Chemistry*, vol. 55 (1983) pp. 1980-1986.

D. Yates, "Spectroscopic Investigations of Gold Surfaces", Journal of Colloid and Interface Science, vol. 29, No. 2, Feb. 1969 (pp. 194-204).

(List continued on next page.)

Primary Examiner—Kenneth M. Schor
Attorney, Agent, or Firm—Finnegan, Henderson, Farabow, Garrett & Dunner

[57] ABSTRACT

In a redox reaction process, the oxidized state of organic compounds is increased through the steps of directing oxides of nitrogen together with a reducing agent selected from oxygenated compounds and aromatic compounds through a catalyst bed in the form of supported gold heated to a temperature sufficient to reduce the oxides of nitrogen present to nitric oxide, after which the higher oxidized forms of organic compounds are recovered. The organic compounds to be oxidized can be separated by chromatography before introduction with one of the oxides of nitrogen into the catalyst bed, and detection of the reducing agent by chemiluminescent measurement of $NO_2^*$ enables determination of the higher oxidized species produced.

10 Claims, 2 Drawing Figures

D. H. Fine et al, "Principle of Operation of the Thermal Energy Analyzer for the Trace Analysis of Volatile and Non-volatile N-Nitroso Compounds", *Journal of Chromatography*, vol. 107, (1975) pp. 351–357.

D. H. Fine et al., "Trace Analysis of Volatile N-Nitroso Compounds by Combined Gas Chromatography and Thermal Energy Analysis", *Journal of Chromatography*, vol. 109, (1975) pp. 271–279.

N. Kashihira et al., "Chemiluminescent Nitrogen Detector-Gas Chromatography and its Application to Measurement of Atmospheric Ammonia & Amines," *Journal of Chromatography*, vol. 239 (1982) pp. 617–624.

METHOD FOR SELECTIVE CONVERSION OF ORGANIC COMPOUNDS AND DETECTING SAME BY GAS CHROMOTOGRAPHY AND CHEMILUMINESCENCE DETECTION

This application is a continuation of application Ser. No. 637,505 filed Aug. 3, 1984, now abandoned.

This invention relates to novel and improved reduction/oxidation or redox reaction processes involving the catalyzed reduction of oxides of nitrogen, and further relates to a method and apparatus for the selective detection of constituents resulting from such redox reaction processes.

BACKGROUND AND FIELD OF THE INVENTION

Numerous processes have been devised for converting certain nitrogen compounds to nitric oxide (NO). Representative of such processes is that disclosed in U.S. Letters Pat. No. 3,919,397 to R. K. Gould in which a gas is passed through a plurality of alumina tubes containing wires of a catalytic material, such as, platinum. The wires are connected to a source of electrical energy for resistively heating the wire in order to speed up the thermal conversion of nitrogen to nitric oxide when passed into contact with the wires. In this and other processes, it is known also that one can detect or measure the concentration of nitric oxide by combining ozone with the nitric oxide to produce nitrogen dioxide ($NO_2$) in an excited electronic state, oxygen and subsequently emitted light. The quantity of light produced is a measurement of the concentration or amount of nitric oxide present and typically is carried out by various types of chemiluminescent detectors. Gould, however, suggests that materials, such as gold, which he asserts are consumed in the reaction with $NO_2$ to produce NO are not properly catalysts. Gould fails to recognize the potential of utilizing gold as a catalyst in redox reaction processes in which certain reducing agents when combined with oxides of nitrogen are capable of being converted to more valuable materials.

Numerous other patents and publications may be found in the literature which disclose a variety of approaches to so-called $NO_x$ converters as well as the use of gas or liquid chromatography and chemiluminescence detectors for measuring resultant products of the reaction. Representative patents are U.S. Letters Pat. Nos. 4,301,114 to D. P. Rounbehler et al, 4,066,409 to D. H. Fine, 3,963,928 and 3,882,028 to W. J. Zolner, and 4,193,963 to W. Bruening et al. Rounbehler et al, for example, is concerned more with a particular form of molecular sieve for trapping species other than NO and $NO_2$ that could interfere with the detection process; and in Fine, organic nitrogen-containing compounds are chromatographically separated, pyrolyzed in contact with oxygen and the nitric oxide emitted from the decomposition is measured.

Other patents pertain to methods and means for catalytic reduction of oxides of nitrogen. For example, U.S. Letters Pat. No. 4,162,235 to G. J. K. Acres et al is directed to a catalytic purification process for exhaust gas in which platinum group metals including gold are associated with one or more base metals to carry out catalytic reduction of oxides of nitrogen in the presence of suitable reducing agents. In U.S. Letters Pat. No. 4,028,274 to H. R. Kunz, various metal catalysts are proposed for use in combination with a support material, such as, a carbon powder and broadly suggests the utilization of gold as a catalyst but not in any specific reaction or pro- cess.

To the best of our knowledge, no one has recognized the ability to carry out a redox reaction, i.e. a reduction oxidation process in which oxides of nitrogen are combined with a reducing agent, such as, alcohols, olefins, aldehydes or other selected organic compounds which can be catalyzed by a heated gold surface to convert the organic compounds selected to new, more valuable, oxidized or dehydrogenated species. A related feature of the present invention resides in the ability to selectively detect the new species by a combination of gas chromatography and chemiluminescent measurement without detecting the presence of other compounds, such as, alkanes, chlorinated hydrocarbons, water, oxygen and nitrogen. Since oxygenated organic compounds typically exist at trace levels in the atmosphere while the alkanes are present at much higher concentrations, this selective process is useful in improving the detection of the oxygenated constituents of the atmosphere as well as in other complex matrices, such as, petroleum and fossil fuel products, beverages, and fragrances.

SUMMARY OF THE INVENTION

It is therefore an object of the present invention to provide for a novel and improved method for selective conversion and upgrading of organic compounds; and further wherein such organic compounds may be efficiently detected in a continuous manner without sensing the presence of other compounds.

Another object of the present invention is to provide for a novel and improved redox reaction process for combining reducing agents, such as, alcohols, aldehydes, ketones, phenols, amines, olefins and aldehydes with oxides of nitrogen to convert the organic compounds to new oxidized or dehydrogenated forms.

It is a further object of the present invention to provide for a novel and improved method and apparatus for the catalyzed reduction of nitrogen dioxide to nitric oxide for subsequent measurement by chemiluminescent reaction with ozone in such a way as to be sensitive to reducing agents, including most oxygenated organic compounds and aromatic compounds, but insensitive to water, the major constituents of air, alkanes and halogenated hydrocarbons.

It is an additional object of the present invention to provide for a novel and improved supported gold surface as a catalyst in a redox reaction process involving oxides of nitrogen with various reducing agents both to facilitate the conversion and upgrading of certain organic compounds to new oxidized species and to form the basis for more efficient, selective detection and recovery of the upgraded compounds produced.

In accordance with the present invention, there has been devised a novel and improved reduction/oxidation process, referred to hereinafter as a redox reaction process, for increasing the oxidized state of organic compounds and comprising the steps of passing oxides of nitrogen in combination with a reducing agent selected from the group consisting of oxygenated compounds, olefins, amines, and aromatic compounds through a confined area containing a catalyst. The catalyst is preferably in the form of supported gold heated to a temperature sufficient to reduce the oxide of nitrogen present to nitric oxide, and followed by recovering the higher oxidized forms of organic compounds produced. A related feature of this invention is to provide a method and means by which the organic compounds to be oxidized can be separated, e.g., by chromatography, in a continuous manner as a preliminary to being introduced together with one of the oxides of nitrogen into the confined area as well as to facilitate detection of these reducing agents by chemiluminescent measurement of product nitric oxide. This method has useful application to the detection of species which appear in the atmosphere as well as in other complex matrices, such as, petroleum and fossil fuel products, beverages and fragrances, and also for the recovery of higher oxidized forms or species resulting from the group consisting of reducing agents, including alcohols, aldehydes, amines, ketones, olefins, and aromatic compounds. A preferred form of apparatus in accordance with the present invention resides in a reactor which comprises in combination a chromatographic column into which the reducing agents are introduced, a conduit leading from an output end of the chromatographic unit having an inlet for the introduction of oxides of nitrogen into the conduit, a catalyst bed including means for heating the bed to an elevated temperature sufficient to reduce said oxides of nitrogen present to nitric oxide and to convert organic compounds present to higher oxidized forms. Nitric oxide analyzer means includes ozone generator means for producing ozone to undergo reaction with the nitric oxide produced by said heated catalyst to form nitrogen dioxide in an excited electronic state whereby to selectively detect the oxidized or dehydrogenated species of the organic compounds by measurement of the nitric oxide produced the reactor after elution from said chromatographic column.

Other objects, advantages and features of the present invention will become more readily appreciated and understood when taken together with the following detailed description of a preferred embodiment in conjunction with the accompanying drawing, in which:

DETAILED DESCRIPTION OF THE PREFERRED EMBODIMENT

Figure 1:
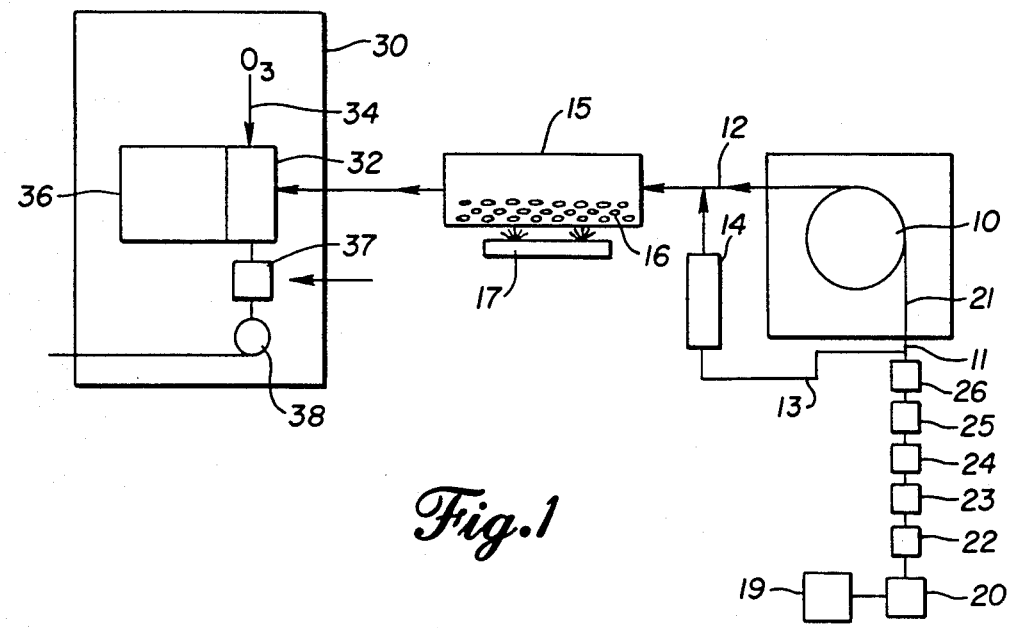
FIG. 1 is a schematic diagram of a preferred form of detector apparatus constructed in accordance with the present invention.

There is shown by way of illustrative example in FIG. 1 of this application a preferred apparatus for the selective detection of constituents after elution from a chromatographic column apparatus represented at 10 and having an injection port 11. The constituents are directed through a main conduit 12 for mixture with nitrogen dioxide in a gas carrier which, for example, may be helium or air from a carrier gas source 13 and is directed into the main conduit 12 via permeation tube 14 containing a source of $NO_2$. The resultant mixture in the conduit 12 is directed into the inlet side of a quartz tube 15 in which is contained a gold catalyst bed as represented at 16. This bed is heated by suitable means 17 to an elevated temperature on the order of 200° C. to 400° C. and may be monitored with a thermocouple, not shown. The constituents which are introduced via the column 10 are typically reducing agents, such as, alcohols, aldehydes, amines, ketones, olefins and aromatic compounds which, when mixed with nitrogen dioxide and passed through the confined area containing the heated catalyst bed 16 will reduce the nitrogen dioxide to nitric oxide.

The apparatus 10 may, for purposes of illustration, be an F&M Model 810 gas chromatograph, having a $\frac{1}{4}''$ by 5' glass column packed with 0.1% SP-1000 on Carbopack C, manufactured and sold by Supelco, Inc., of Bellefonte, Pennsylvania, or a fused silica capillary column (HP-Ultra, 20 meters long, 0.3 mm inner diameter, coated with cross-linked polydimethylsiloxane, film thickness 0.5 $\mu$m, manufactured and sold by Hewlett-Packard Company, Avondale, Pennsylvania. Retention times of compounds may be established using a flame ionization detector or other conventional detectors. When the ionization detector is removed, the redox detector is connected via a glass or Teflon ® transfer line which is installed between the column 10 and the $NO_2$ makeup gas tee from the tube 14. This transfer line may be resistively heated to a temperature on the order of 50° C. and may introduce up to on the order of 6 ml of dead volume. The flow of the carrier gas and entrained $NO_2$ may, for example, be maintained at 25 ml per minute. Concentrations of $NO_2$ in the make-up gas can be varied by changing the temperature of the porous Teflon ® permeation tube 14 which acts as a reservoir for liquid $NO_2$. Typically, a few parts per million of $NO_2$ in the make-up gas stream is more than sufficient to oxidize the organic compound in the effluent from the chromatography column. The chromatographic column 10 is useful in the present invention for the purpose of rapidly separating those volatile compounds rn a mixture which will be oxidized in reducing the nitrogen dioxide to nitric oxide.

For instance, the following compounds or elements do not produce NO: water, carbon dioxide, oxygen, helium, nitrogen, argon, dichloromethane, acetonitrile, n-pentane, n-hexane, n-decane, 1,2-dichloroethane, cyclohexane, chloroform and tetrachloroethene. The following compounds or elements do produce NO and therefore are selectively detected by this redox system: hydrogen, acetone, 2-butanone, 4-methyl-2-pentanone, methanol, ethanol, n-propanol, n-butanol, formaldehyde, acetaldehyde, propanal, n-butanal, n-pentanal, n-hexanal, formic acid, acetic acid, n-propanoic acid, n-butanoic acid, benzene, toluene, benzaldehyde, hydrogen peroxide, 2-hexene, n-butyl ether, cyclohexene 1-methylcyclohexene, ammonia and carbon monoxide.

Solutions of hexanal in dichloromethane and a five component mixture of n-butanal, ethyl acetate, n-butanol, benzene and 4-methyl-2-pentanone in dichloromethane were injected into the gas chromatographic system, separated by the gas chromatographic column and detected by the catalytic redox production of NO from $NO_2$. Ethyl acetate represents an intermediate class of compounds which only partially react under the conditions typically used (temperature, flow rate, etc.), the partial reaction ($\sim$1–10%) generating a response at least an order of magnitude less than the other responsive compounds. Compound concentrations ranged from 0.5 $\mu$g/$\mu$l to 2 $\mu$g/$\mu$l and 0.4 $\mu$l to 1.0 $\mu$l of solution were injected.

Linearly extrapolated detection limits for the packed column system described herein are approximately 40 ng of ethanol, methanol, benzene, 4-methyl-2-pentanone, and hexanal, and 300 ng of n-butanal. Using capillary columns and reducing the system dead volume has improved the detection limit by more than an order of magnitude. Using a capillary column creates narrower compound peaks, which also allows more sensitive detection. For example, with a capillary column 10, 0.1 ng of n-octanol, n-decanol, 2,6-dimethylphenol and 2,6-dimethylaniline can be detected.

At the catalyst bed, one suitable form of supported gold is formed by 10 grams of ½ mm diameter borosilicate glass beads introduced to an aqueous solution of 0.1 gram $HAuCl_4 \cdot 3H_2O$. This solution is evaporated to dryness, then further dried at 110° C. for two hours at 0.5 torr. The gold coated beads are then reduced to elemental gold under a flowing $H_2$ atmosphere at 300° C. for two hours. Two grams of gold coated glass beads 16 are then placed in a 6 mm diameter quartz tube 15 with silanized glass wool plugs to form the 10 cm long active catalyst bed. The catalyst is heated resistively to 300° C. and the temperature monitored with a thermocouple.

For the purpose of illustration, a typical gas handling system may consist of bottled air from a gas carrier source 19 which is passed through a series of traps to insure a minimum amount of impurities. As shown, a 13X molecular sieve trap 20 is positioned in inlet line 21 to remove water vapor and a Hopcalite ® chamber 22 serves to remove carbon monoxide. An in line UV ozonizer 23 creates ozone to oxidize NO to $NO_2$ in a 500 mL holdup reaction volume 24. $NO_2$ and $CO_2$ are removed by an Ascarite trap 25, and residual ozone may be scrubbed by activated charcoal, not shown. A final 4A molecular sieve trap 26 is used to remove $SO_2$ and hydrocarbons thereby to asure the supply of high purity air or helium for the entire system, including the nitrogen dioxide permeation tube chamber 14 via a split tee 13.

A nitric oxide analyzer takes the form of a chemiluminescence detector 30 which for purposes of illustration may be a Thermo Electron Corporation Model No. 14D dual channel chemiluminescence $NO/NO_x$ analyzer. The analyzer is modified by installation of a valve to isolate the molybdenum $NO_x$ catalyst, allowing the instrument to serve as a single channel NO detector without depleting the molybdenum catalyst. Flow through the instrument reaction chamber as represented at 32 is maintained by a metal bellows pump 38 and regulated by a flow restrictor capillary, not shown, which also serves to reduce the pressure in the chamber 32 for improved light emission. An internal electric discharge ozone generator as represented at 34 directs ozone through a capillary restrictor, not shown, to the reaction chamber 32 which is mounted directly in front of the photomultiplier tube 36. The photomultiplier tube 36 detects the chemiluminescence emitted from the $NO_2$ which is produced in an excited electronic state, or $NO_2^*$, by the subsequent reaction of ozone with the NO produced from the reactions in the heated catalyst bed. Then upon relaxation of the $NO_2$ from an excited state, according to the reaction scheme: $NO+O_3 \rightarrow NO_2^* \rightarrow NO_2+h\nu$, light is emitted which can be measured continuously with a photomultiplier tube and photon counting techniques. Higher oxidized species which are formed as a result of the reduction of $NO_2$ are recovered through a cold trap designated at 37.

The following examples are presented by way of illustration and not limitation for a further understanding of the features and aims of the present invention:

EXAMPLE 1

Alcohols were converted to aldehydes by reaction with nitrogen dioxide at gold surfaces heated at approximately 300° C. A gold catalyst bed was prepared which consisted of glass beads upon which gold was coated from gold chloride aqueous solutions by already well-established techniques. For example, ten grams of borosilicate glass beads approximately 0.5 mm in diameter was added to an aqueous solution containing 0.1 gram of $HAuCl_4 \cdot 3H_2O$. The solution was evaporated to dryness, then the beads were further dried at 110° C. for two hours at 0.5 torr. The gold salt-covered beads were then treated by heating at 300° C. for 2 hours under a flowing hydrogen stream to form a layer of elemental gold on the surfaces of the glass beads. Two grams of gold coated beads were then placed in a quartz tube with a 6 mm outer diameter and a 4 mm inner diameter. The beads were held in place in the tube to form a 10 cm long catalyst bed with small porous end plugs made of silanized glass wool. The catalyst bed is heated typically at temperatures between 200° C. and 400° C. and the temperature is maintained constant at an optimal value determined by considerations of the rates of the reaction which, as expected, are faster at higher temperatures, vs. energy consumption and thermal stability of reactants and products, the latter factors favoring the use of lower temperatures.

A carrier gas which does not participate in the reaction was used to move reactants and products through the catalyst bed in one-pass tests. Helium is generally used for analytical applications, but nitrogen or air or the reactants themselves can also be used as a carrier to facilitate transport. In this example, bottled compressed air was first passed through a trap containing Linde 13x molecular sieves to remove water and other impurities, then through a Hopcalite ® trap to remove carbon monoxide. An in-line ultraviolet light ozone generator caused oxidation of NO to $NO_2$. Any $NO_2$ and $CO_2$ present were then removed by passing the air stream through an Ascarite trap. Residual ozone was removed by a bed of activated charcoal. A final bed of Linde 4A molecular sieve was used to remove $SO_2$ and any other organic compound impurities remaining in the air stream.

This purified air stream with a flow-rate of 10 standard cubic centimeters per minute was then passed through a thermostated chamber (25° C.) with a Teflon ® permeation tube containing nitrogen dioxide and its dimer. The permeation tube was a porous Teflon ® polymer sealed at both ends and, at 25° C., was calibrated gravimetrically to have an emission rate of 10.2 $\mu$g/min of $NO_2$.

Flow through the system was maintained by a metal bellows pump at the outlet and a flow restrictor glass capillary (0.5 mm i.d.) at the exit of the catalyst bed. Total augmented air flow was one L/min when the pressure in the catalyst bed was 630 torr. The calculated linear velocity through the bed was 130 cm/sec, so the mean residence contact time in the catalyst bed was less than 0.1 sec. Longer residence times can be used at some sacrifice in throughput, but even with these short catalyst contact times conversion of several compounds was accomplished with high yields (greater than 90%). When 0.37 $\mu$g of 1-pentanol was injected into the carrier gas stream entering the catalyst bed heated at 399° C., the products were collected with a Tenax ® polymeric sorbent. Thermal desorption of the sorbed samples with cryogenic focusing at the inlet of a capillary chromatography column and subsequent gas chromatographic/mass spectrometric analysis revealed that no unreacted 1-pentanol was detected and that the alcohol was converted in excellent yield to the aldehyde, 1-pentanal. Nitric oxide was formed as the expected product from reducing nitrogen dioxide. The formation of nitric oxide was confirmed by chemiluminescence measurements upon reaction with ozone, as previously described.

EXAMPLE 2

In the same apparatus, with similar conditions to those described in Example 1, the gold-catalyzed redox process involving the reaction of 4-methyl-2-pentanol with $NO_2$ was studied. When 0.38 μg of 4-methyl-2-pentanol was injected and the reaction products analyzed after a single pass through the reactor, the only oxidation product that could be detected by gas chromatography/mass spectrometry was the ketone, 4-methyl-2-pentanone. In Example 1, a primary alcohol was converted to the corresponding aldehyde, while this Example shows that secondary alcohols are oxidized to form the corresponding ketone by the following reaction:

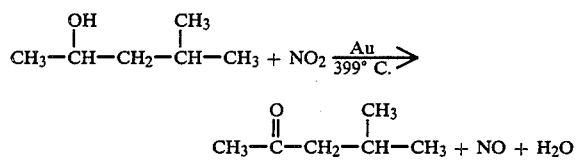

The process has utility in both synthesis and analysis. When a ketone is desired from a secondary alcohol the above reaction can be conducted. If desired, the NO formed as a reaction product can be reconverted to $NO_2$ by reaction with oxygen or air at an elevated temperature and recycled.

To be useful analytically as a sensor or chromatography detector the novel process can be combined by the well-established reaction with ozone to constitute a new selective detection system. For example, an alcohol eluted from a chromatographic column can be passed through the catalyst bed to form NO in the reaction described above. NO can be detected by chemiluminescence upon mixing with ozone as described above.

EXAMPLE 3

Another experiment using the same apparatus and conditions similar to the above examples was performed using cyclohexene as the starting material. In this instance, the catalyzed dehydrogenation process yielded benzene. Unlike the earlier two examples, however, there was a substantial amount of the starting material left after the single pass reaction process under the flow, temperature and concentration conditions used. This experiment demonstrated that olefins can be dehydrogenated by $NO_2$ catalytically to form less saturated products, and that olefins can be detected by chemiluminescence measurement of the NO formed.

EXAMPLE 4

With the same apparatus and under nearly the same conditions detailed in Example 1, we studied the gold-catalyzed reaction of a ketone, 4-methyl-2-pentanone, with nitrogen dioxide. After one pass of a 2.5 μg sample of 4-methyl-2-pentanone a small amount of 4-methyl-3-pentene-2-one, giving rise to about 3% of the total ion chromatogram of the effluent from the catalyst bed was formed. Most of the effluent was identified as unreacted starting material. This experiment demonstrated that ketones are dehydrogenated by $NO_2$ catalytically to form unsaturated ketones, and that ketones can be detected by chemiluminescent measurement of the NO formed.

EXAMPLE 5

Another example of the invention represents a preferred embodiment for use as a chromatographic detector for analysis of mixtures of compounds:

Small glass beads were used as the catalyst bed. One gram of 230-325 mesh borosilicate glass beads was added to an aqueous solution of 0.5 grams of $HAuCl_4 \cdot 3 H_2O$. These beads were further treated in a manner similar to that in Example 1. Fifteen milligrams of gold-coated glass beads were placed in a glass tube of 1.8 mm inner diameter and 6 mm outer diameter. The catalyst bed was 0.7 cm long and was heated as in Example 1. The chromatographic system used was an F&M Model 810 gas chromatograph, equipped with a 20 meter long by 0.31 mm diameter fused silica capillary column, with a 0.52 μm film thickness of cross-linked polydimethylsiloxane manufactured by Hewlett-Packard Company of Avondale, Pennsylvania.

Since this is an analytical separation application, a closed gas flow system consisting of purified helium was used to carry $NO_2$ from the permeation tube into the catalytic reduction chamber. Helium was also used as the chromatographic carrier gas, at a flow rate of approximately one milliliter per minute. A separate helium source supplied 30 to 150 milliliters per minute, at 10 psig, to the nitrogen dioxide permeation device described in Example 1. This nitrogen dioxide-doped helium flow was added to the effluent of the gas chromatographic column just prior to entering the heated catalyst bed. A minimum length of Teflon ® tubing, with a volume of 1 milliliter or less, connected the exit of the catalyst bed directly to the chemiluminescence reaction chamber.

When a mixture of approximately twenty nanograms each of ten different compounds (n-decane, n-octanol, 2,6-dimethylphenol, 2,6-dimethylaniline, napthalene, n-decanol, n-tridecane, methyl decanoate, n-tetradecane and methyl undecanoate) was injected into the gas chromatograph, only five of the compounds were selectively detected using the redox reaction system of this invention. The five compounds, n-octanol, n-decanol, naphthalene, 2,6-dimethylaniline and 2,6-dimethylphenol, were oxidized, reducing nitrogen dioxide to nitric oxide, which was detected downstream by chemiluminescence upon mixing with ozone. By contrast, the alkanes (decane, tridecane and tetradecane) gave no response, and the two methyl esters (methyl decanoate and methylundecanoate) gave intermediate responses. In flame ionization detectron, all ten compounds will produce responses.

EXAMPLE 6

Another experiment using the same apparatus and conditions described in Example 5 was performed using a commercially available perfume sample sold under the trademark Esteé Lauder, Private Collection (pure undiluted fragrance). From a comparison of a flame ionization detector chromatogram with a chemiluminescent detector as described, the differences in the number of peaks and in relative peak heights illustrated the selective discrimination between different compounds by the chemiluminescent detector.

EXAMPLE 7

Apparatus similar to that described in Example 5 was modified to divert one-half of the flow exiting the analytical gas chromatographic column and directed to a standard flame ionization detector. The remaining half of the gas flow proceeded unaffected through the heated catalyst bed as in Example 5. An auxiliary source of helium, approximately 2 ml per minute, was supplied at the point where the flow was split in order to maintain the same linear gas velocity to both detectors.

Figure 2:
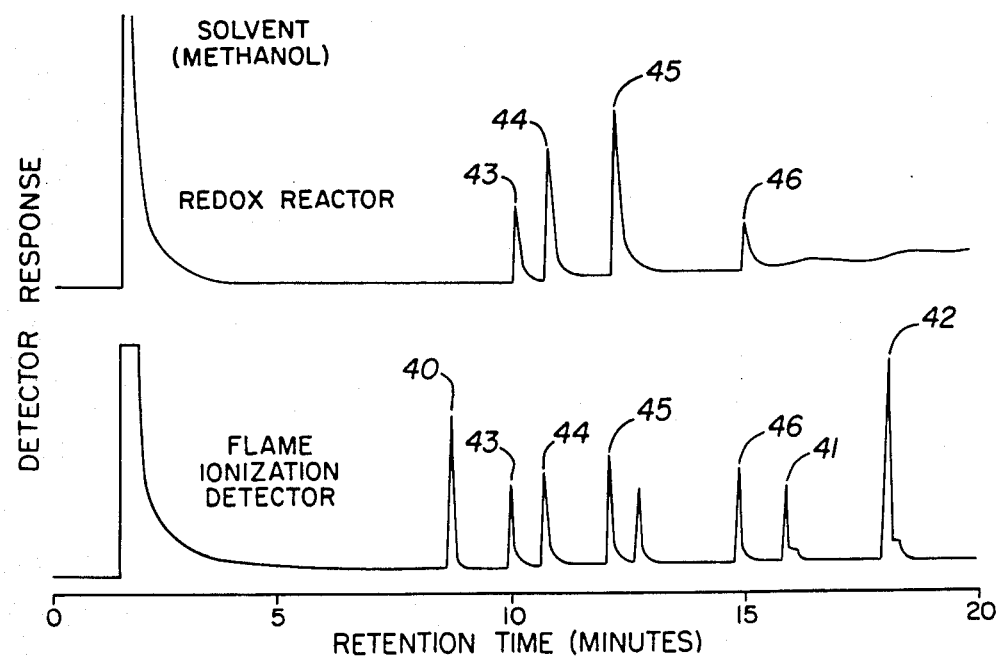
FIG. 2 illustrates representations of chromatograms produced by the detectors in accordance with Example 5.

FIG. 2 illustrates a representative pair of chromatograms produced by this parallel detector arrangement, the bottom trace showing the same ten components identified in Example 5, and the upper trace demonstrating the selective detection achieved. Accordingly, this arrangement permitted direct comparison of components eluted from the chromatographic column in terms of retention time and relative response for the novel redox chemiluminescent detector versus a standard flame ionization type detector. This Example demonstrates the advantage of using the redox detector coupled with other detectors either in parallel or in series. For example, chromatograms produced by this parallel detector arrangement demonstrated that the redox detector is selective and exhibited no chromatographic peak at the retention times of n-decane 40, n-tridecane 41 and n-tetradecane 42 which were detected by the flame ionization detector. Further, the peak heights and areas were different for each of the compounds to which the redox detector responded when compared with the peak heights and areas measured by the flame ionization detector. For instance, the peak areas were nearly the same for n-octanol 43 as measured by either detector while the peaks drawn from the signals of the redox detector were larger for 2,6-dimethylphenol 44 and 2,6-dimethylaniline 45 but smaller for n-decanol 46 than those from the flame ionization detector. The ratios of the carriers can be used to help identify or confirm the identity of unknown compounds by comparing peak area ratios with those from authentic known standard samples. This process of employing parallel detectors as described greatly enhanced the power of chromatographic analysis based on retention data.

Examples 3 and 4 demonstrated that, even when there are no easily oxidizable functional groups present, our novel process can yield products of dehydrogenation. It appears that the hydrogens being removed must be activated by a functional group, however, because saturated hydrocarbons such as n-hexane do not react with $NO_2$ at gold surfaces to give any detectable nitric oxide (or presumably any organic oxidation or dehydrogenation products). This forms the basis for the selectivity of sensors and chromatographic detectors based on the novel gold-catalyzed redox reaction process coupled with chemiluminescence following the reaction of nitric oxide with ozone. Under the conditions chosen, no detectable reaction occurs at gold surfaces between nitrogen dioxide and n-alkanes, chlorinated hydrocarbons, nitrogen, oxygen, water, argon, acetonitrile or carbon dioxide. By contrast, compounds that can be readily oxidized or dehydrogenated, such as, alcohols, aldehydes, carboxylic acids, phenols, amines, esters, aromatic compounds, ammonia, hydrogen peroxide, carbon disulfide, and hydrogen undergo gold-catalyzed reaction with $NO_2$. These oxidation/dehydrogenation processes are more selective and specific than most presently used processes based upon, for example, reaction with oxygen, and therefore have utility for synthesis. Concurrently, use of this redox process forms the basis for chromatographic detection systems that are more selective than most commonly used detectors, allowing detection of trace species of interest in the presence of much larger concentrations of less interesting or less significant compounds, such as, saturated or chlorinated hydrocarbons, water, oxygen and carbon dioxide. Furthermore, our new process makes it possible to detect species, such as, ammonia and hydrogen which cannot be measured sensitively with commonly used chromatography detectors such as the hydrogen flame ionization detector.

From the foregoing, it is apparent that substitutions of nitrogen dioxide with nitric acid or other oxides of nitrogen with higher oxidation states than nitric oxide are envisioned as equivalent in the process of catalytic reductions to form NO. Moreover, it is apparent from Example 5 that samples containing high concentrations of large numbers of alkanes could be analyzed for phenols, alcohols, amines and other easily oxidized or dehydrogenated species with greater efficacy and accuracy and with fewer interferences from the alkanes or other non-reactive compounds with the redox chemiluminescence detection system of this invention than by flame ionization detection.

The redox reaction chamber, coupled with a chemiluminescence detector, can be attached to any typical gas chromatographic system in place of any existing detector, or in series with a non-destructive detector. The redox reactor incorporates a heated catalyst bed with provision for adding sufficient make-up gas doped with reactant $NO_2$ gas. While gold surfaces in several different forms can catalyze reaction of $NO_2$ to form NO, the catalyst demonstrated to be most effective consists of elemental gold supported on small glass beads and packed in a hollow quartz tube as described. Other types of gold surfaces show varying degrees of effectiveness. The novel redox process can also be used as a detector for constituents in the effluents of liquid chromatography or supercritical fluid chromatography columns, if the effluents are contacted with nitrogen dioxide at heated gold surfaces.

It is therefore to be understood from the foregoing that various modifications and changes may be made in the process of the present invention as herein set forth and described without departing from the spirit and scope thereof, as defined by the appended claims.

We claim:

1. A process for the detection of organic compounds comprising:

catalyzing a heterogeneous phase reduction-oxidation reaction between a nitrogen oxide oxidizing agent, selected from the group consisting of nitric acid and nitrogen dioxide, and a compound capable of reducing said oxidizing agent to nitric oxide, said reducing compound being selected from the group consisting of alcohols, aldehydes, amines, ketones, phenols, olefins, aromatic compounds, and oxygen, sulphur, nitrogen and phosporous-containing compounds of the foregoing and mixtures thereof, in the presence of a solid elemental gold catalyst, whereby said reducing compound is oxidized to a more highly unsaturated, dehydrogenated oxidation state and nitric oxide is thereby produced;

recovering said nitric oxide;

contacting said recovered nitric oxide with ozone, whereby chemiluminescence is emitted; and detecting the emitted chemiluminescence whereby the measure of light provides an indication of the amount of said reducing compound.

2. The process of claim 1, wherein said catalyst is heated to a temperature sufficient to catalyze said reduction-oxidation reaction.

3. The process of claim 2, wherein said reduction-oxidation reaction is conducted at a temperature of about 200° C. to 400° C.

4. The process of claim 2, wherein said catalyst is in the form of supported gold metal.

5. The process of claim 4, wherein said catalyst is in the form of gold coated glass beads placed in a quartz tube.

6. The process of claim 1, further comprising the step of chromatographically separating the organic compounds prior to said reduction-oxidation reaction.

7. The process of claim 6, wherein said chromatographic separation is accomplished by a technique selected from the group consisting of gas chromatography, liquid chromatography and super-critical fluid chromatography.

8. The process of claim 7, wherein said chromatographic separation is conducted in a continuous flow.

9. The process of claim 1, wherein said reducing compound and said oxidizing agent react in the vapor phase.

10. The process of claim 1, wherein said reducing compound and said oxidizing agent react in the liquid phase.

* * * * *